United States Patent
Sinn et al.

(10) Patent No.: US 6,306,367 B1
(45) Date of Patent: *Oct. 23, 2001

(54) FLUORESCENT CONJUGATE FOR DIFFERENTIATING BETWEEN DISEASED AND HEALTHY TISSUES

(75) Inventors: Hansjörg Sinn, Wiesloch; Wolfgang Maier-Borst, Dossenheim; Gerd Stehle, Mannheim; Michael Kaus, Heidelberg; Andreas Wunder, Eppelheim; Hans-Hermann Schrenk, Zeiskamm, all of (DE)

(73) Assignee: Deutsches Krebsforschungszentrum Stiftung des offentlichen Rechts, Heidelberg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/117,253

(22) PCT Filed: Jan. 23, 1997

(86) PCT No.: PCT/DE97/00166

§ 371 Date: Nov. 19, 1998

§ 102(e) Date: Nov. 19, 1998

(87) PCT Pub. No.: WO97/26920

PCT Pub. Date: Jul. 31, 1997

(30) Foreign Application Priority Data

Jan. 23, 1996 (DE) .................................. 196 02 295

(51) Int. Cl.⁷ .............................. A61K 49/00; C07K 1/00
(52) U.S. Cl. ........................ 424/9.6; 424/9.61; 530/363
(58) Field of Search ............................ 424/9.6, 9.61; 435/125; 436/172, 800, 88; 600/317; 514/776; 530/363; 549/223

(56) References Cited

U.S. PATENT DOCUMENTS

| 4,213,904 | 7/1980 | Haugland ................. 260/326.5 |
| 5,232,684 | * 8/1993 | Blumberg et al. ............... 424/1.1 |
| 5,308,604 | * 5/1994 | Sinn et al. ...................... 424/1.53 |
| 5,589,154 | * 12/1996 | Anderson ...................... 424/1.41 |

OTHER PUBLICATIONS

Biochemicallien Organische Verbindungen Voor Research En Diagnositca, 1994, Sigma®, NL pp. 68, 71 and 344.
Bieniarz, C. et al. "Thiolate and Phosphorothioate Functionalized Fluoresceins and Their use as Fluorescent Labels", *Bioconjugate Chemistry*—5(1):31–39 (1994).
Dalesandro, M.R. et al., "Temporal Variations in the Fine Specificity of IgM Anti–Fluorescyl Antibodies", *Immunol. Cell Biol.* —69(4):243–251 (1991).
Moore, C.H. et al., "Synthesis of Erythrosin Isothiocyanate and its use as a Phosphorescent Depolarization Probe for Slow Rotational Mobility of Membrane Proteins", *Biochem. Soc. Trans.* —7(5):945–946 (1979).
Rushfeldt, C. et al., "Distribution of Colon Cancer Cells Permanently Labelled by Lectin–Mediated Endocytosis of a Trap Label", *Cancer Research* —53:658–662 (1993).
Speirs A. et al., "Segmental Motion and Rotational Diffusion of the $Ca^{2+}$—Translocating Adenosine Triphosphatase of Sarcoplasmic Reticulum, Measured by Time–Resolved Phosphorescence Depolarization", *Biochem J.* —213(1):67–74 (1983).
Watt, R.M. et al., "Affinity Labeling of Antifluorescyl Antibodies", *Chemical Abstracts* 100 23): Abstract No. 190020 (1984).
Watt, R.M. et al., "Fluorescein Hapten: An Immunological Probe/Appendix B", pp 177–181 State Univ. of New York; Upstate Medical Center; Syracuse NY; USA (1984).
Yan, C. et al., "Characterization and Morphological Analysis of Protein–Loaded Poly (Lactide–co–Glycolide) Microparticles Prepared by Water–in–Oil–in–Water Emulsion Technique", *Journal of Controlled Release*, 32 (3):231–241 (1994).

* cited by examiner

*Primary Examiner*—Michael G. Hartley
(74) *Attorney, Agent, or Firm*—Albert P. Halluin; Viola T. Kung; Howrey Simon Arnold & White, LLP

(57) ABSTRACT

The present invention relates to conjugates comprising a compound capable of emitting fluorescence, a linker and a protein. The present invention also concerns the preparation of such conjugates as well as their use.

6 Claims, 1 Drawing Sheet

R = H (aminofluorescein (AFl)).
= Br (aminoeosin yellowish (AEs)).
= I (aminoerythrosin (AEros)).

FLUORESCENT CONJUGATE FOR DIFFERENTIATING BETWEEN DISEASED AND HEALTHY TISSUES

The present application is a United States national stage pursuant to 35 U.S.C. §371 of PCT application PCT/DE97/00166 filed on Jan. 23, 1997.

FIELD OF THE INVENTION

The present invention relates to conjugates for distinguishing unhealthy or pathological tissue from healthy tissue, a process for the preparation of such conjugates as well as their use.

BACKGROUND OF THE INVENTION

When pathological tissue is treated, its removal is often an essential step. For this purpose, it is necessary for the operating surgeon to understand clearly where pathological tissue ends and healthy tissue begins. However, this is often impossible. Therefore, spurs of pathological tissue are overlooked which then represent the basis for new formation of the pathological tissue.

Thus, it is an object of the present invention to provide a method of making a distinction between pathological tissue and healthy tissue.

BRIEF DESCRIPTION OF THE INVENTION

According to the invention, this is achieved by the subject matter defined in the claims.

Therefore, the present invention relates to a conjugate comprising a fluorescence-capable compound or a compound capable of emitting fluorescence, a linker and a protein.

The expression "fluorescence-capable compound or a compound capable of emitting fluorescence" includes compounds of any kind that can be stimulated to emit fluorescence. Examples include fluorescent dyes, e.g. xanthene dyestuffs such as fluorescein, aminofluorescein (AFl), erythrosin, aminoerythrosin (AEros), eosin yellowish and 2-aminoeosin yellowish (AEs) as well as derivatives and analogues thereof. The above compounds may also have photodynamic activity. An example thereof is AEros. The photodynamic activity is typically stimulated at a wavelength ranging from 500 to 550 nm (AEros: 533 nm). Porphyrins, chlorins and bacteriochlorins are normally exempted from the above compounds.

A conjugate according to the invention may contain several compounds that are capable of emitting fluorescence and may be the same or different from one another.

A protein, such as a particularly native protein that is not considered exogenous, may be present in a conjugate according to the invention. The protein preferably has a molecular weight of up to 100,000 daltons, particularly 30,000 to 100,000 daltons. In especially preferred embodiments, the protein is albumin, particularly human serum albumin (HSA), and transferrin. It is also possible to use protein fragments. Like the proteins, protein fragments may effect a concentration of the conjugate in pathological tissues, particularly in tumor tissue and in superficial relatively small vessels, e.g. neovascularizations in the region of the cornea (keratoderma of the eye).

The term "linker" comprises compounds of any kind that are suited to link the compound capable of emitting fluorescence and the protein. Linkers are preferably not cleaved in the body. Examples of such linkers are cyanuric chloride (Cy) and derivatives thereof.

The components of a conjugate according to the invention may be given as educts. In the conjugate, they are present in derivatized form. Preferred conjugates according to the invention are shown in FIG. 1.

Conjugates according to the invention may be prepared according to conventional processes by which the compound capable of emitting fluorescence, the linker and the protein are bonded, preferably covalently, with one another. In this connection, reference is made to the preparation of the conjugates of Examples 1 to 3 by way of example.

Conjugates according to the invention preferably have an increased half life in the organism. In addition, conjugates according to the invention preferably concentrate in pathological tissues, particularly in tumor tissue and in superficial, relatively small vessels, e.g. neovascularizations in the region of the cornea. Compounds capable of emitting fluorescence are stimulated by light, e.g. a UV lamp, so as to make visible pathological tissues, whereas healthy tissue in which the conjugates according to the invention do not concentrate are not made visible. Therefore, it is possible to delimit pathological tissues from healthy tissue.

Furthermore, the conjugates according to the invention may be stimulated to develop a photodynamic activity at a wavelength ranging from 500 to 550 nm. Light having this wavelength has only a low penetration depth in the body. Thus, the conjugates according to the invention are suited in the best possible manner to treat superficial pathological tissues, e.g. neovascularizations and esophageal tumors.

DETAILED DESCRIPTION OF THE INVENTION

The following examples explain the invention. They are only exemplary, and the invention is not intended to be limited thereby.

EXAMPLE 1

Preparation of the AEros-Cy-HSA Conjugate According to the Invention

Figure 1:
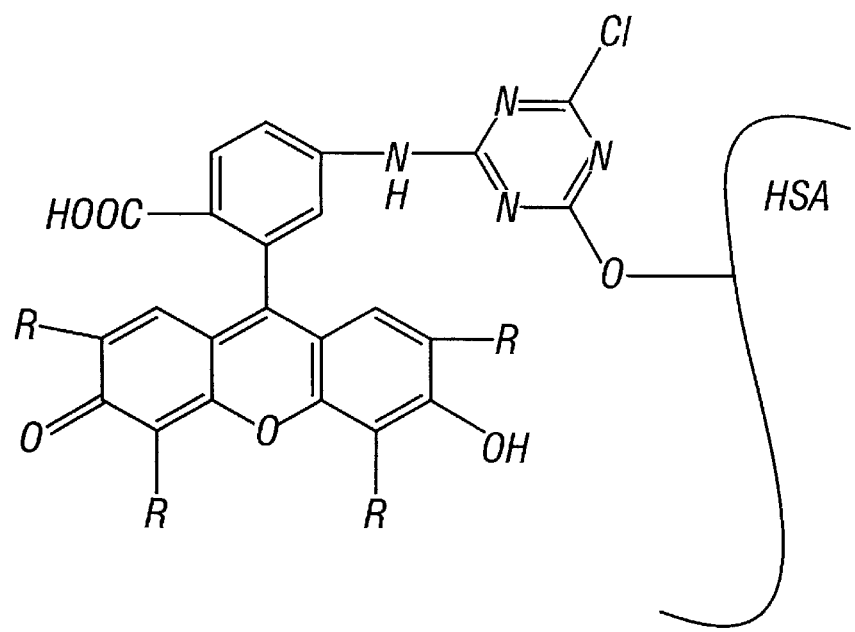
FIG. 1: depicts the AEs-Cy-HSA, AEros-Cy-HSA and AFl-Cy-HSA conjugates according to the invention.

AEros-Cy-HSA is shown in FIG. 1. 50 mg 5([4,6-dichlorotriazine-2-yl]amino)fluorescein (AFl-Cy) was dissolved in 5 ml DMSO and reacted to form AEros-Cy by adding a corresponding amount of iodosuccinimide in 2 ml DMSO and 1 ml 0.17 M Bic (sodium bicarbonate). The reaction was terminated after a few seconds. The AEros-Cy prepared in this way was slowly added with constant stirring to 4 g HSA dissolved in 20 ml of original solution, 20 ml. Bic and 20 ml DMSO. The solution adopted a deep-red color. It remained clear. After about 45 minutes, the protein solution was diluted with 11 of distilled water and then purified by ultrafiltration (YM 30, Amicon). The analytical purity control was made by means of HPLC. The AEros-Cy-HSA conjugate according to the invention was obtained.

EXAMPLE 2

Preparation of the AES-Cy-HSA Conjugate According to the Invention

AEs-Cy-HSA is shown in FIG. 1.
AEs-Cy-HSA was prepared according to the process described in Example 1.
Bromosuccinimide was used in place of iodosuccinimide.

EXAMPLE 3

Preparation of the AFl-Cy-HSA Conjugate According to the Invention

AFI-Cy-HSA is shown in FIG. 1.

45 mg AFl-Cy was dissolved in 4 ml DMSO and slowly added with constant stirring to 4 g HSA dissolved in 20 ml of original solution, 20 ml Bic and 20 ml DMSO. The solution adopted an intensely yellow color during the AFlCy addition. It remained clear. After about 45 minutes, the resulting solution was diluted using 1l of distilled water and subsequently purified by ultrafiltration (YM 30, Amicon). Purity was controlled by means of HPLC. AFl-Cy-HSA was obtained.

EXAMPLE 4

Concentration of AFl-Cy-HSA in a tumor

Figure 2:
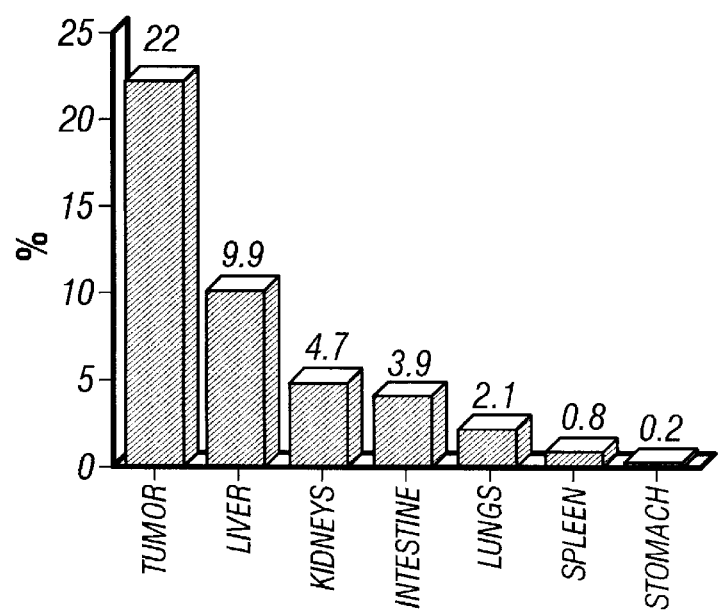
FIG. 2: depicts the concentration of AFl-Cy-HSA in tumor tissue.

A rat (240 g) having a Walker 256 carcinosarcoma (tumor weight 4.2% of the body weight) was given an intravenous injection of AFl-Cy-HSA of Example 4, which was labeled radioactively beforehand. The rat was killed after 24 hours. All organs and the tumor were removed. The amounts of conjugate disposed in the organs and in the tumor were determined by measuring the radioactivity. As shown in FIG. 2, the AFl-Cy-HSA conjugate according to the invention concentrated in the tumor.

What is claimed is:

1. A conjugate consisting essentially of a fluorescent dye, at least one linker and native human serum albumin, wherein the linker is cyanuric chloride, and said conjugate is suitable for in vivo use in distinguishing unhealthy or pathological tissue from healthy tissue.

2. The conjugate according to claim 1, wherein the fluorescent dye is a xanthene dyestuff.

3. The conjugate according to claim 2, wherein the xanthene dyestuff is selected from the group consisting of fluorescein, aminofluorescein, erythrosin, aminoerythrosin, eosin yellowish and aminoeosin yellowish.

4. The conjugate according to claim 1 or 3, wherein the fluorescent dye has photoactivity.

5. The conjugate according to claim 1 or 3, wherein said conjugate consists essentially of more than one fluorescent dye.

6. A method for preparing a conjugate according to claim 1 or 3, comprising the steps of: covalently binding the fluorescent dye, the linker and the native human serum albumin.

* * * * *

UNITED STATES PATENT AND TRADEMARK OFFICE
CERTIFICATE OF CORRECTION

PATENT NO.    : 6,306,367 B1
DATED         : October 23, 2001
INVENTOR(S)   : Sinn et al.

It is certified that error appears in the above-identified patent and that said Letters Patent is hereby corrected as shown below:

<u>Title page,</u>
Item [75], Inventors, delete "Zeiskamm," and insert -- Zeiskamm;
Dirk Hoff-Biederbeck, Großniedesheim; --.

Signed and Sealed this

Nineteenth Day of August, 2003

JAMES E. ROGAN
*Director of the United States Patent and Trademark Office*